US00PP21858P2

(12) United States Plant Patent
Egger

(10) Patent No.: US PP21,858 P2
(45) Date of Patent: Apr. 5, 2011

(54) ***HEUCHERA* PLANT NAMED 'MIDNIGHT BAYOU'**

(50) Latin Name: ***Heuchera* hybrid**
Varietal Denomination: Midnight Bayou

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 51 days.

(21) Appl. No.: 12/653,618

(22) Filed: Dec. 14, 2009

(51) Int. Cl.
*A01H 5/00* (2006.01)

(52) U.S. Cl. ..... Plt./440

(58) Field of Classification Search ..... Plt./440
See application file for complete search history.

*Primary Examiner* — Kent L Bell

(74) *Attorney, Agent, or Firm* — Klarquist Sparkman, LLP

(57) ABSTRACT

A new and distinct hybrid of *Heuchera* plant characterized by its very large purple spring leaves to rose-purple summer leaves with black veins and a silver veil. In addition it has a large mounding habit and excellent vigor.

2 Drawing Sheets

Botanical denomination: *Heuchera* hybrid.
Variety designation: 'Midnight Bayou'.

BACKGROUND OF THE INVENTION

The present invention relates to a new and distinct cultivar of *Heuchera* and given the cultivar name of 'Midnight Bayou'. *Heuchera* is in the family Saxifragaceae. *Heuchera* 'Midnight Bayou' originated from a cross between *Heuchera* 796-1, a proprietary non-commercial hybrid, as the seed parent, and *Heuchera* 827-1, a proprietary non-commercial hybrid, as, as the pollen parent.

Compared to the seed parent, *Heuchera* 796-1, the new cultivar has purple rather than dark brown leaf color.

Compared to the pollen parent, *Heuchera* 827-1, the new cultivar has much larger leaves, that are also purple but less veiled, taller flower stalks, and a bigger habit.

Compared to *Heuchera* 'Berry Smoothie' (U.S. Plant patent application Ser. No. 12/653,628), the new cultivar has leaves that are dark purple with black veins rather than rose purple. The leaves of 'Midnight Bayou' are somewhat smaller.

This new *Heuchera* is uniquely distinguished by its very large purple spring leaves to rose-purple summer leaves with black veins and a silver veil. In addition it has a large mounding habit and excellent vigor.

This new cultivar has been reproduced only by asexual propagation (tip cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 2 shows close up of the fall color of the new variety in November in Canby, Oreg.

FIG. 3 shows a young planting of the new variety in the garden in September in Canby, Oreg.

DETAILED PLANT DESCRIPTION

Figure 1:
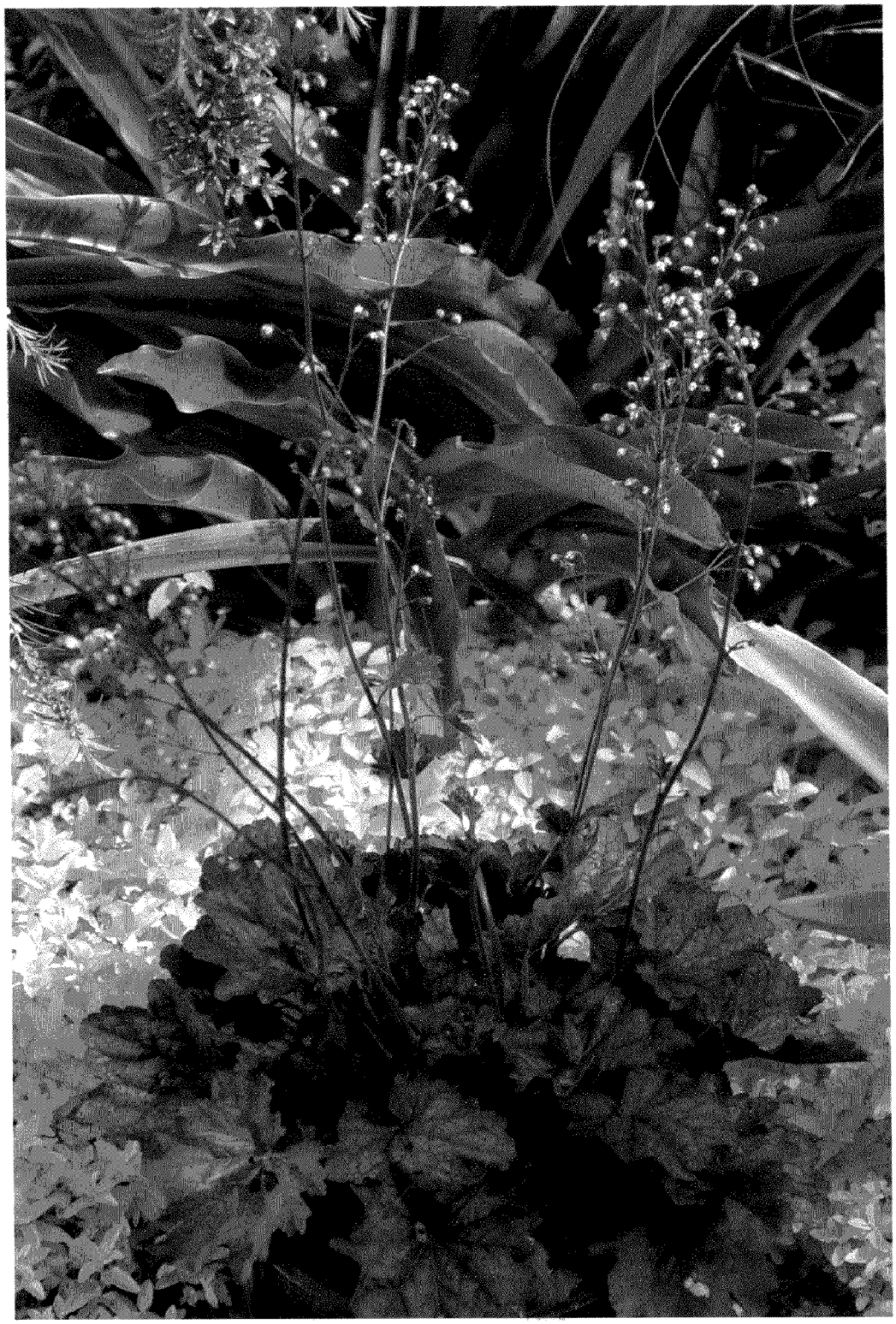
FIG. 1 shows a 1-year-old plant of *Heuchera* 'Midnight Bayou' in flower growing in a one gallon container in May Canby, Oreg.

The following is a detailed description of the new *Heuchera* cultivar based on observations taken in October of a ten-month-old specimen growing in the ground in the trial bed in full sun and with added irrigation in the summer months in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart, 1999 edition.

Plant:

- *Form.*—Basal rosette, herbaceous perennial.
- *Hardiness.*—USDA Zone 4 to 9.
- *Size.*—24 cm tall from top of the foliage to the ground and 55 cm wide.
- *Habit.*—Mounding.
- *Vigor.*—Excellent.
- *Roots.*—Fibrous, freely branching, fine, and white in color; roots develop easily from tip cuttings.

Leaf:

- *Type.*—Simple.
- *Arrangement.*—Rosette.
- *Shape.*—Broadly ovate.
- *Lobing/division.*—7 shallow lobes, the terminal is usually the longest; shallow secondary lobes.
- *Venation.*—Palmate.
- *Margins.*—Broadly crenate and somewhat undulate.
- *Apex.*—Mucronulate.
- *Base.*—Cordate, lobes overlapping at the base.
- *Blade size.*—Grows to 12.5 cm long and 12 cm wide.
- *Texture.*—Leathery.
- *Surface texture.*—Glandular on both sides.
- *Petiole description.*—Grows to 17 cm long and 4 mm wide, glandular hairs, Greyed Purple 187B.

*Leaf color.*—Topside, spring leaves are a two toned purple, topside Greyed Purple 187A with Purple 71A interveinally and bottom side closest to Greyed Purple 187A, mature summer leaves are between Red Purple 72A and Greyed Purple 186B with veins Black 202A, new fall leaves topside are Red Purple 59A with veins Black 202A; bottom side, from Red Purple 59A on young leaves to a color closest to Greyed Purple 187B on mature leaves.

Inflorescence:

*Size.*—Grows to 8 cm wide and 16 cm long.

*Type.*—Thyrse.

*Number of flowers per thyrse.*—About 80.

*Number of thyrse.*—15.

*Peduncle.*—Grows to 77 cm tall, but usually 55 cm long, 5 mm wide at base, Greyed Purple 187A, glandular hairs, with 1 to 5 petiolate cauline leaves (blades ovate to orbicular, grows to 5.5 cm long and 5 cm wide. 7 lobed, incised margin, acute, cordate and overlapping, between Red Purple 72A and Greyed Purple 186B with veins Black 202A).

*Pedicel.*—Variable in size, with glandular hairs, Greyed Purple 187A.

*Bloom period.*—Late June through October in Canby, Oreg.

Flower bud:

*Size.*—3 mm wide and 5 mm long.

*Description.*—Glandular puberulent, ovoid.

*Color.*—Red Purple 59B on bottom half and Red Purple 59D on the top half tipped with Red Purple 59A (sometimes with lines of White 155D where the lobes meet).

Flower:

*Type.*—Perfect.

*Shape.*—Campanulate.

*Size.*—7 mm long and 4.5 mm wide.

*Corolla description.*—5 in number, extruding, 3.8 mm long and 1 mm wide, spatulate, tip acute, margin entire, glandular on both sides, White 155D on both sides with tip Red Purple 59D.

*Calyx description.*—Campanulate, 7 mm long and 4.5 mm wide, with 5 lobes divided ⅔ way to the base, each 2.5 mm wide and 4 mm long, glandular hairs outside and inside, tips acute, margin entire; bicolor, inside and outside bottom ⅓ Red Purple 59C, middle ⅓ Red Purple 63D, top ⅓ Red Purple 63D with Red Purple 59B in the middle of each lobe.

*Stamen description.*—5 in number, filaments 2 mm long, White 155D, anthers sterile, 1 mm, Orange Red 35B.

*Pistil description.*—1, 2-beaked, 4 mm long; ovary 1.8 mm long, Green White 157A; style 2.2 mm long, Green White 157D, stigma Green White 157D.

*Fragrance.*—None.

*Lastingness.*—Each thyrse blooms for about 2 weeks on the plant.

Fruit:

*Type.*—Two beaked capsule.

*Size.*—7 mm deep by 3 mm wide.

*Fertility.*—Good.

*Color.*—Brown 200D.

Seed:

*Shape.*—Linear.

*Size.*—1 mm long.

*Color.*—Black 202A.

Pest and disease tolerance: Excellent disease resistance to powdery mildew, the common problem of *Heuchera*. Susceptible to *Heuchera* rust and root weevils.

I claim:

1. A new and distinct *Heuchera* plant as herein illustrated and described.

* * * * *

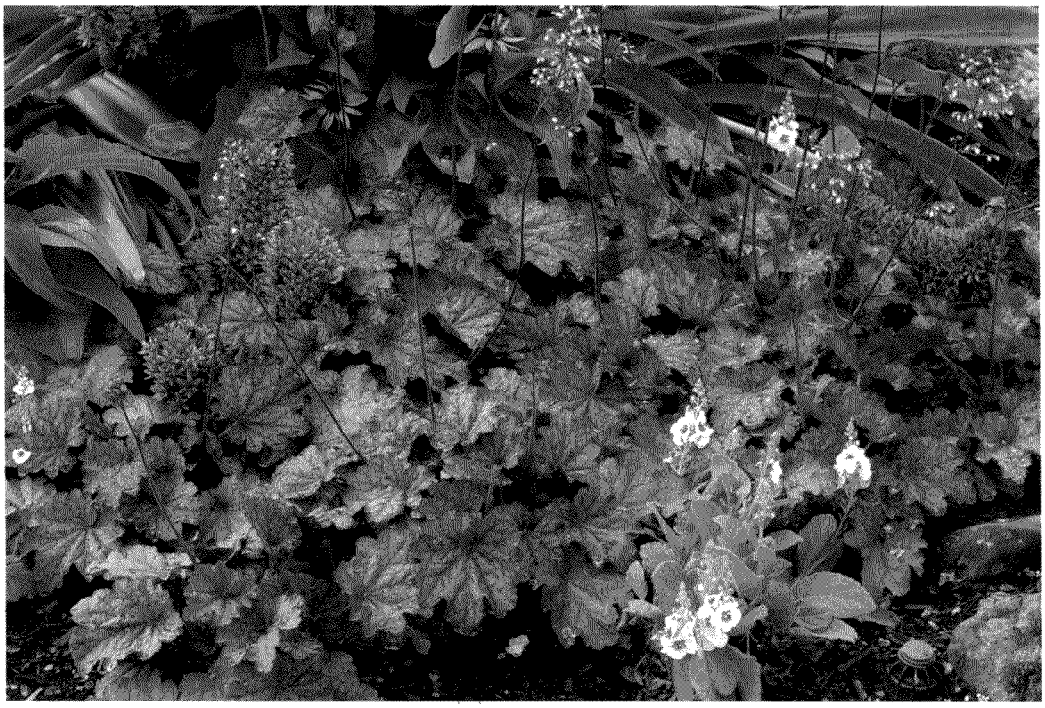

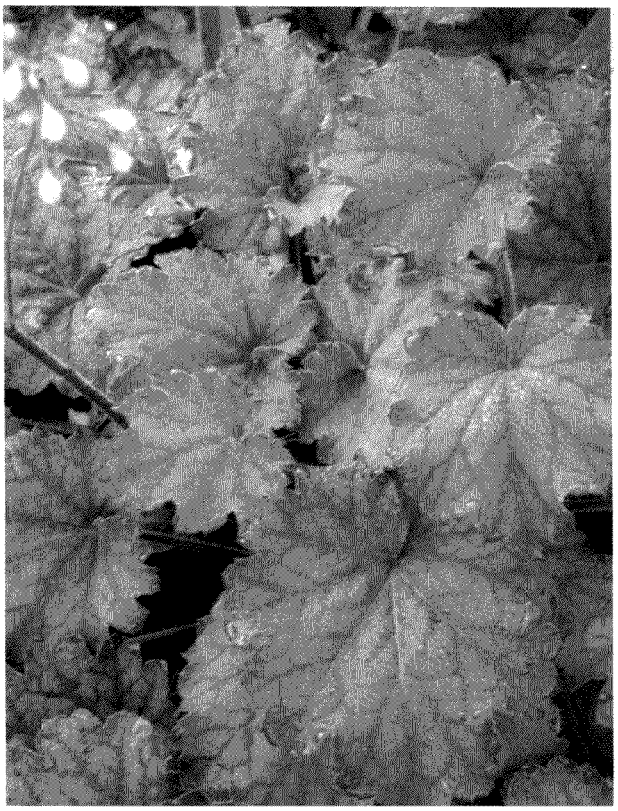
Figure 2 above, Figure 3 below